US010960401B2

(12) United States Patent
Hortsch et al.

(10) Patent No.: US 10,960,401 B2
(45) Date of Patent: Mar. 30, 2021

(54) PROCESS FOR THE DECOMPOSITION OF BIOMASS MATERIAL

(71) Applicant: CLARIANT INTERNATIONAL LTD., Muttenz (CH)

(72) Inventors: Ralf Hortsch, Munich (DE); Thomas Hoppe, Landshut (DE); Bjoern Huehnlein, Straubing (DE)

(73) Assignee: Clariant International Ltd., Muttenz (CH)

( * ) Notice: Subject to any disclaimer, the term of this patent is extended or adjusted under 35 U.S.C. 154(b) by 753 days.

(21) Appl. No.: 15/645,001

(22) Filed: Jul. 10, 2017

(65) Prior Publication Data

US 2017/0320970 A1 Nov. 9, 2017

Related U.S. Application Data

(63) Continuation-in-part of application No. PCT/EP2015/079986, filed on Dec. 16, 2015.

(30) Foreign Application Priority Data

Jan. 16, 2015 (EP) .................................... 15000112

(51) Int. Cl.
*B02C 23/00* (2006.01)
*B02C 23/06* (2006.01)
(Continued)

(52) U.S. Cl.
CPC .............. *B02C 23/00* (2013.01); *A23K 10/12* (2016.05); *A23K 10/32* (2016.05); *B02C 23/06* (2013.01);
(Continued)

(58) Field of Classification Search
CPC .......... B09B 3/00; B09B 3/0041; B09B 5/00; C08H 8/00; C12P 7/08; C12P 7/10;
(Continued)

(56) References Cited

U.S. PATENT DOCUMENTS 5,370,999 A * 12/1994 Stuart ...................... C08H 8/00
435/105
6,159,335 A * 12/2000 Owens ................... D21C 9/004
162/100
(Continued)

FOREIGN PATENT DOCUMENTS

CN  102602913 A  7/2012
CN  103525502 A  1/2014
(Continued)

OTHER PUBLICATIONS

Pejó.; Realistic approach for full-scall bioethanol production fro lignocellulose: a review: Journal of Scientific & Industrial Research, Nov. 2008, vol. 67, pp. 874-884.
(Continued)

*Primary Examiner* — Shelley M Selfqq
*Assistant Examiner* — Katie L. Parr
(74) *Attorney, Agent, or Firm* — Verrill Dana LLP

(57) ABSTRACT

A process for the decomposition of biomass-material includes subjecting a lignocellulose-containing biomass-material to comminution, subjecting the comminuted lignocellulose-containing biomass-material to a sifting to separate from the comminuted lignocellulose-containing biomass-material a fraction of small-particles, and subjecting the remaining comminuted lignocellulose-containing biomass-material to a pretreatment. Before, during, or after the pretreatment, small particles can be added to the remaining comminuted lignocellulose-containing biomass-material. Optionally, the small particles can be added continuously during the pretreatment. The addition of small particles decreases friction of the remaining comminuted lignocellulose-containing biomass-material results in decreased process time, energy savings, and reduced production costs.

12 Claims, 2 Drawing Sheets

(51) Int. Cl.
- B02C 23/14 (2006.01)
- B02C 23/08 (2006.01)
- A23K 10/12 (2016.01)
- A23K 10/32 (2016.01)
- C12P 7/08 (2006.01)
- C08B 1/00 (2006.01)
- B09B 3/00 (2006.01)
- C08H 8/00 (2010.01)
- C12P 7/10 (2006.01)
- C08B 37/00 (2006.01)
- B09B 5/00 (2006.01)
- B08B 5/00 (2006.01)
- C12P 7/00 (2006.01)

(52) U.S. Cl.
CPC ............. B02C 23/08 (2013.01); B02C 23/14 (2013.01); B09B 3/00 (2013.01); B09B 3/0041 (2013.01); B09B 5/00 (2013.01); C08B 37/0057 (2013.01); C08H 8/00 (2013.01); C12P 7/08 (2013.01); C12P 7/10 (2013.01); C08B 1/00 (2013.01); C12P 7/00 (2013.01); C12P 2201/00 (2013.01); Y02E 50/10 (2013.01)

(58) Field of Classification Search
CPC ........ C12P 2201/00; C08B 1/00; Y02E 50/16; Y02E 50/17; B02C 9/00; B02C 9/02; B02C 9/04; B02C 11/06; B02C 11/08; B02C 23/06–10; B02C 23/14–16; C21B 1/02; C21B 1/021; C21B 1/06–10
USPC ....................... 241/6, 9, 13, 22, 24.1, 25, 28
See application file for complete search history.

(56) References Cited

U.S. PATENT DOCUMENTS

| | | | |
|---|---|---|---|
| 7,910,338 B2 * | 3/2011 | Hennessey | C12P 7/08 435/99 |
| 2010/0105119 A1 * | 4/2010 | Medoff | C10G 32/00 435/161 |
| 2010/0219271 A1 * | 9/2010 | Russell | C10J 3/506 241/24.1 |
| 2011/0111456 A1 * | 5/2011 | Medoff | B01J 19/085 435/68.1 |
| 2012/0012031 A1 * | 1/2012 | Husband | D21C 9/001 106/204.3 |
| 2012/0104123 A1 * | 5/2012 | White | C10L 5/366 241/3 |
| 2012/0187228 A1 * | 7/2012 | Camp | D21C 3/02 241/30 |
| 2013/0217073 A1 * | 8/2013 | Chundawat | C08H 8/00 435/99 |
| 2016/0369305 A1 * | 12/2016 | Piriou | B03C 7/006 |

FOREIGN PATENT DOCUMENTS

| | | |
|---|---|---|
| CN | 104194857 A | 10/2014 |
| WO | 2009158709 A2 | 12/2009 |

OTHER PUBLICATIONS

Vandenbossche, et al.; A new lignocellulosic biomass deconstruction process combining thermo-machano chemical action and bio-catalytic enzymatic hydrolysis in a twin-screw extruder; Elsevier—Industrial Crops and Products, 2014, vol. 55, pp. 258-266, XP055186133.

Chang, et al.; Lime Pretreatment of Crop Residues Bagasse and Wheat Straw; Appliied Biochemistry and Biotechnology, 1998, pp. 135-159, XP008087461.

Shaw, et al.; Physiochemical characteristics of densified untreated ad steam exploded poplar wood and wheat straw grinds; Elsevier—Biosystems Engineering, 2009, vol. 103, pp. 198-207, XP026096313.

Maas, et al.; Pilot-scale conversion of lime-treated wheat straw into bioethanol: quality assessment of bioethanol and valorization of side streams by anaerobic digestion and combustion; BioMed Central—Biotechnology for Biofuels, 2008, vol. 1, issue 14, pp. 1-13, XP021045778.

Chang, et al.; Lime Pretreatment of Switchgrase: Applied Biochemistry and Biotechnology; 1997, vol. 63-65, pp. 3-19, XP002902194.

Mosier, et al.; Features of promising technologies for pretreatment of lignocellulosic biomass; Elsevier—Bioresource Technology, 2005, pp. 673-686, vol. 96, XP027800661.

International Search Report, dated Feb. 24, 2016, that issued in PCT/EP2015/079986.

HORIBA Scientific, A Guidebook to Particle Size Analysis, 2020, HORIBA Instruments, Inc. Irvine, California, 32 pgs.

* cited by examiner

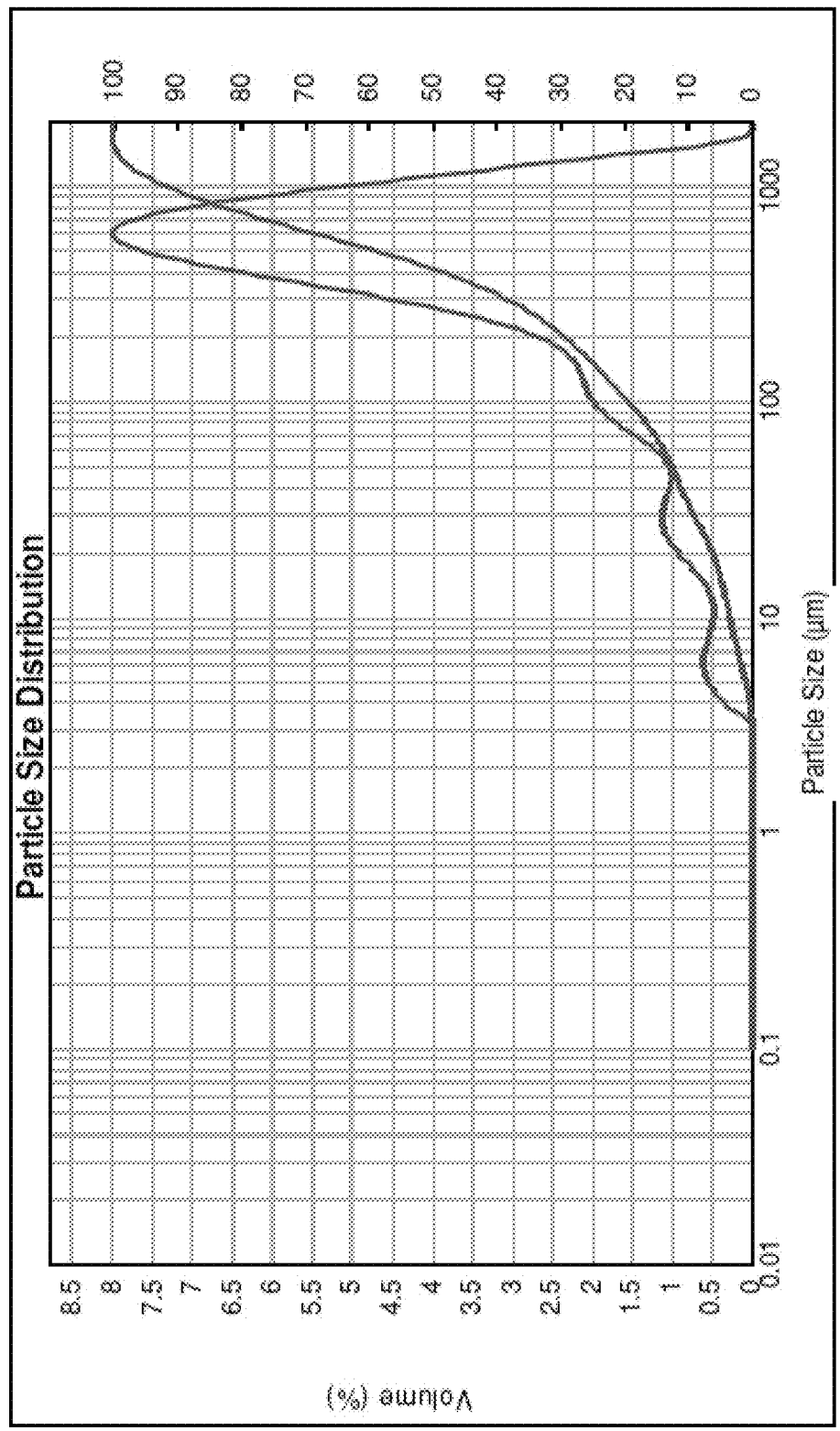

PROCESS FOR THE DECOMPOSITION OF BIOMASS MATERIAL

CROSS REFERENCE TO RELATED APPLICATIONS

This application claims the priority of PCT/EP2015/079986, filed on 16 Dec. 2015, which claims priority to European Patent Application No. 15000112.1, filed on 16 Jan. 2015, the entire contents of each of which are hereby incorporated in total by reference

FIELD OF THE INVENTION

The present application pertains to a process for the decomposition of lignocellulose-containing biomass-material

BACKGROUND OF THE INVENTION

Due to limited resources of mineral oil and demands to reduce CO2 emissions the chemical industry seeks more sustainable production routes for the manufacture of commodity chemicals such as liquid fuels and base chemicals. Part of that strategy focuses on the conversion of lignocellulosic biomass into versatile chemicals or fuels such as ethanol. Lignocellulosic biomass contains cellulose (~25-40% w/w d.s.), hemicellulose (~15-25% w/w d.s.) and lignin (~15-30% w/w d.s.) as major components and minor amounts of other carbohydrates, waxes, proteins and inorganic compounds. Among forms of plant biomass, lignocellulosic biomass derived from any forestry and agricultural waste streams, such as wood residues and cereal straw are particularly well suited for conversion to commodity chemicals and fuels because of their availability, low cost and environmentally sound production. Additionally, life cycle analyses of production processes utilising lignocellulosic feedstocks indicate reduced greenhouse gas emissions compared to processes based on other feedstocks.

Various process options that describe the conversion of lignocellulosic biomass to ethanol and other base chemicals have been described (Pejo et al., 2008). To realize these processes on an industrial scale it is particularly desirable to transfer the maximal amount of energy, carbon and mass content contained in the renewable feedstock to the end products. At present none of the described conversion processes have realised this to the full extent.

Exemplary unit operations for the biotechnological conversion of lignocellulosic material (e.g. straw) to value-adding products (e.g. ethanol) are: mechanical de-sizing and/or physicochemical pretreatment, enzymatic hydrolysis, fermentation and product recovery.

Regarding industrial scale cellulosic ethanol production, one key barrier is still the expenditure for cost and thus a low-energy process and efficient biomass conversion are of major importance.

Therefore, the object of the present invention is the provision of an improved highly efficient process for the decomposition of lignocellulose-containing biomass-material.

BRIEF DESCRIPTION OF THE DRAWINGS

FIG. 2 shows the volumetric particle size distribution of the particles added to the pretreated biomass as described in example 1

DESCRIPTION OF THE INVENTION

Figure 1:
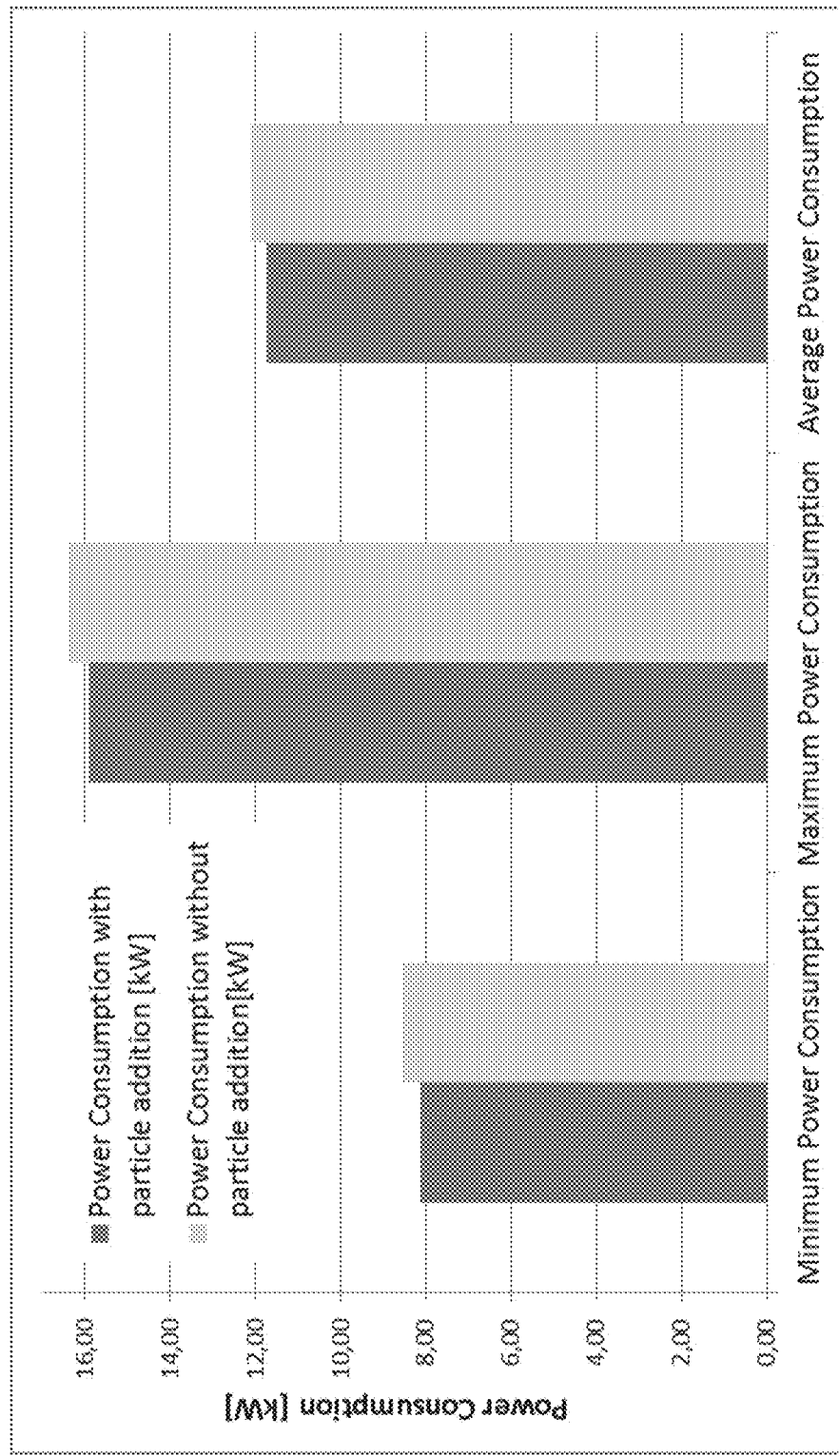
FIG. 1 shows power consumption when carrying out the method with and without sifting and particle addition

The inventors of the present invention have now surprisingly found that this object of the present invention may be achieved by a process for the decomposition of lignocellulose-containing biomass-material, comprising the steps
(a) providing lignocellulose-containing biomass-material;
(b) subjecting the lignocellulose-containing biomass-material to comminution;
(c) subjecting the comminuted lignocellulose-containing biomass-material to a sifting to separate a particle-fraction consisting of particles with an average particle diameter of less than 2500 µm;
(d) subjecting the remaining comminuted lignocellulose-containing biomass-material to a pretreatment;
wherein before, during or after pretreatment particles are added to the lignocellulose-containing biomass-material wherein at least 70 wt.-% of the particles have an average particle diameter of less than 1.6 mm.

Within the present invention the term "biomass-material" is a "lignocellulose-containing material". The term "lignocellulose-containing material" is to be understood to comprise all kind of material known to a person skilled in the art as comprising lignocellulose. Terms "lignocellulose-containing material", "lignocellulose-containing biomass", "lignocellulosic material" and "lignocellulosic biomass" are to be understood as synonyms within the present invention. In one embodiment lignocellulose-containing material according to the present invention includes wood, cereal straw and/or husks, bagasse, oat hulls, switch grass, cellulose, raw paper pulp (obtained from pulp and paper production) and mixtures thereof. Alternative sources or additional components may comprise one or more of the following components: purified cellulose, pulp, milk whey, molasses or sugars such as glucose and lactose. In one embodiment the lignocellulose-containing material contains at least 25 wt.-%. In alternative embodiments the lignocellulose-containing material contains:
 at least 40 wt.-%;
 at least 70 wt.-%;
 at least 80 wt.-%; or
 at least 90 wt.-% lignocellulose.

It is to be understood that the lignocellulose-containing material may also comprise other compounds such as proteinaceous material, starch, sugars, such as fermentable sugars and/or non-fermentable sugars.

According to step b) of the process according to the present invention, the provided lignocellulose-containing biomass-material is subjected to a comminution. The term "comminution" is thereby understood to comprise any kind of comminution known to a person skilled in the art as suitable for the inventive purpose. Within at least one embodiment, the comminution comprises any kind of mechanical processing, maceration, shredding, grinding, chopping, crushing, cutting, irradiation, milling such as dry milling, wet milling and vibratory ball milling, and any combinations thereof. Within one embodiment the comminution comprises or consists of milling. In one embodiment, this milling is carried out by a hammer-mill. In one embodiment the comminution is carried out in a continuous fashion.

According to step c) of the inventive process, the comminuted lignocellulose-containing biomass-material is subjected to a sifting to separate a particle-fraction consisting of particles with an average particle diameter of less than 2500 µm. In alternative embodiments the average particle diameter is:
- less than 2200 µm;
- less than 1800 µm;
- less than 1600 µm;
- less than 1200 µm; or
- less than 800 µm.

In an alternative embodiment, a particle-fraction consisting of particles with an average particle diameter of from 1 to 2500 µm is separated within step c) of the inventive process. In varying alternative embodiments, the particle-fraction that is separated within step c) of the inventive process is
- 1 to 1800 µm;
- 1 to 1600 µm; or
- 1 to 1200 µm.

In a further embodiment within this separation step c), at least 65% (wt. separated particle fraction/wt. initial biomass-material) of the particles are separated with the respective average particle diameter as defined before. In alternative embodiments, the separation is:
- at least 75% (wt./wt.);
- at least 85% (wt./wt.);
- at least 95% (wt./wt.);
- at least 99% (wt./wt.); or
- 100% (wt./wt.).

Separating particles with an average particle diameter of less than 1200 µm is particularly advantageous as general dust exposure and particularly the risk of dust explosion are significantly minimized. In alternative embodiments, the present invention provides for separating particles with an average particle diameter of:
- less than 1100 µm;
- less than 1000 µm;
- less than 800 µm;
- less than 300 µm; or
- less than 100 µm Within the present invention the term "sifting" is to be understood as comprising any kind of separation of the respective particle fraction—as defined before—known to a person skilled in the art as suitable for the inventive purpose. Within at least one embodiment, the term "sifting" is to be understood as "sieving" and/or "filtrating". In certain embodiments the sifting is carried out within a process wherein during comminution the respective particle fraction as defined before comprising or mainly consisting of particles light enough to stay in the air are carried to a filter or sieve by pneumatic air or aspiration to separate the respective fraction according to step c) of the inventive process. Within one embodiment, the respective particle fraction is separated during comminution—thus steps b) and c) are carried out concurrently. In at least one embodiment, steps b) and c) are carried out in a continuous fashion—or right after comminution. In at least one embodiment comminution is also carried out in a continuous fashion.

In at least one embodiment, the separation according to step c) of the inventive process is carried out in a continuous fashion during comminution of the lignocellulose-containing biomass-material.

According to step d) of the inventive process, the remaining lignocellulose-containing biomass-material is subjected to a pretreatment. The term "remaining lignocellulose-containing biomass-material" is to be understood as comprising any lignocellulose-containing biomass-material not separated within the particle-fraction with an average particle diameter of less than 2500 µm within step c) of the inventive process.

Within the present invention the term "pretreatment" is to be understood as a process leading to at least partial removal and separation of hemicellulose from cellulose and disruption and removal of the lignin sheath, in order to decrease the crystallinity of cellulose and thus to increase the accessible surface area of cellulose and/or to increase the pore size of cellulose. The pretreatment preferentially mobilises the pentose fraction of the lignocellulose-containing material, while at the same time it enhances the digestibility of the solid cellulose-containing fraction.

Methods suitable for the pretreatment of the lignocellulose-containing material according to step (a) of the present invention include any kind of mechanical, biological, chemical and/or physical pretreatment methods known to a person skilled in the art. Within at least one embodiment, the pretreatment method is selected from the methods of mechanical comminution, treatment with acids and/or alkalines, wet oxidation, pH-controlled hydrothermolysis and/or steam explosion.

"Steam explosion" according to the present invention comprises a pressurised hydrothermal treatment. In alternative embodiments, this pressurised hydrothermal treatment is at a temperature of:
- from 60 to 350° C.;
- from 80 to 300° C.;
- from 100 to 250° C.; or
- from 110 to 220° C.

of the lignocellulose-containing material in the absence or presence of acid (such as $H_2SO_4$, HCl, $H_3PO_4$) or base/alkaline (i.e. $NH_4OH$, NaOH, KOH, lime) catalysts, which are added at concentrations from 0.01 to 15% (wt./wt.). In varying embodiments the concentration is:
- from 0.05 to 12.5% (wt./wt.);
- from 0.1 to 10% (wt./wt.); or
- from 0.25 to 7.5%.

In one embodiment of the present invention the pressure is selected from 1 to 100 bar. In various embodiments, the pressure is:
- from 2 to 50 bar;
- from 3 to 25 bar; or
- from 5 to 15 bar.

Reaction times during steam explosion are to be selected from 10 s to 2 h. In alternative embodiments, selected times are:
- from 1 minute to 1.5 hours; or
- from 5 minutes to 1 hour to provide for efficient transformation of the biomass components in preparation for enzymatic hydrolysis.

Within one embodiment a "mechanical comminution" pretreatment of the lignocellulose-containing material is carried out before or during the steam explosion pretreatment, wherein the mechanical comminution is selected from the group consisting of mechanical processing, grinding, shredding, chopping, crushing, cutting, irradiation, milling and combinations thereof.

"Acid pretreatment" according to the present invention constitutes a continuous dilute and/or mild acid treatment, such as, treatment with sulfuric acid, or another organic acids, such as acetic acid, citric acid, tartaric acid, succinic acid, hydrogen chloride or mixtures thereof. Other acids may also be used. A "mild acid treatment according to the present invention is to be understood as carried out at a pH of from 1 to 5 (respective to the lignocellulose-containing material). In alternative embodiments the mild acid treatment is carried out at a pH of from 2 to 3 (respective to the lignocellulose-containing material). In a one embodiment the acid is added in concentrations from 0.01 to 15 wt.-% (wt./wt.). In alternative embodiments, the acid is added in concentrations from:
  0.05 to 12.5 wt.-% (wt./wt.);
  0.1 to 10 wt.-% (wt./wt.) or
  0.25 to 7.5 wt.-%.
In at least one embodiment the acid is sulfuric acid. The acid may be contacted with the lignocellulose-containing material at a temperature in the range of from 120 to 280° C. In alternative embodiments, this range is from 135 to 225° C. or from 150 to 200° C. for a period from 1 to 60 minutes. In alternative embodiments the time period is 2 to 30 minutes or from 5 to 15 minutes. Addition of strong acids, such as sulphuric acid, may be applied within certain embodiments to remove hemicellulose.

"Chemical pretreatment" according to the present invention also pertains to treatment of the lignocellulose-containing material with $H_2O_2$, ozone, Lewis acids, $FeCl_3$, $(Al)_2SO_4$ in aqueous alcohols, glycerol, dioxane, phenol, ethylene glycol, NaOH, $Na_2CO_3$ and/or ammonia. Concentrations, temperature and duration are chosen analogous to the conditions referenced above regarding acid pretreatment.

"Wet oxidation pretreatment" according to the present invention involves the use of oxidizing agents, such as sulphite based oxidizing agents.

The term "mechanical comminution" regarding the "pretreatment" refers to any mechanical treatment which promotes the separation and/or release of cellulose, hemicellulose and/or lignin from lignocellulose-containing material. Examples of mechanical comminution include mechanical processing, grinding, chopping, shredding, crushing, cutting, irradiation, milling such as dry milling, wet milling and vibratory ball milling, and combinations thereof.

"Biological pretreatment" according to the present invention refers to any biological pretreatment which promotes the separation and/or release of cellulose, hemicellulose, and/or lignin from the lignocellulose-containing material. Biological pretreatment techniques can involve applying lignin-solubilizing microorganisms such as actinomycetes (e.g. *Streptomyces* strains), white rod fungi.

Pretreatment methods suitable for the process of the present invention are to be carried out within suitable devices known to a person skilled in the art. A device suitable for carrying out chemical pretreatment may be any kind of vessel such as a batch reactor. A device suitable for carrying out steam explosion may be any kind of vessel such as a batch reactor but may also be carried out within a screw reactor. In at least one embodiment a continuous screw reactor is used.

In varying embodiments the solids content of the pretreated lignocellulose-containing material is:
  up to 75% (wt./wt.);
  from 25 to 65% (wt./wt.); or
  from 40 to 55% (wt./wt.).

Within the process according to the present invention before, during or after pretreatment particles are added to the lignocellulose-containing biomass-material wherein at least 70 wt.-% of these particles have an average diameter of less than 1.6 mm. In alternative embodiments, these particles have an average diameter of:
  less than 1.4 mm;
  less than 1.0 mm; or
  less than 0.75 mm.
In an additional embodiment, at least 80 wt.-% of these particles have an average diameter of less than 1.6 mm. In alternative embodiments: at least 85 wt.-%, at least 90 wt.-%, at least 95 wt.-% or at least 99 wt.-% have an average diameter of less than 1.6 mm. In alternative embodiments the average particle size at each of the provided wt.-% (at least 80 wt.-%, at least 85 wt.-%, at least 90 wt.-%, at least 95 wt.-% or at least 99 wt.-%) is less than 1.4 mm, less than 1.0 mm or less than 0.75 mm.

The inventors of the present invention surprisingly found that the addition of particles of the respective average diameter as defined before improves the conveying of the lignocellulose-containing biomass-material during pretreatment which is particularly beneficial when the lignocellulose-containing biomass-material is conveyed during pretreatment by use of screw or spiral conveyors. The addition of these particles decreases the friction of the material within the treatment device and during conveying through pipelines and thus contributes to the saving of energy but also decreases process time contributing significantly to reduce production costs.

The term "average particle diameter" refers to the D(0.50) value of a volumetric particle size distribution. The D(0.50) value describes the particle size of a volumetric particle size distribution where 50% of the particles are either smaller or larger than the respective value.

In one embodiment of the present invention, the particles are added in a continuous fashion during the pretreatment. It is, however, also possible to add these particles batch-wise. In certain embodiments this would be done at the beginning and/or the middle of the pretreatment.

In one embodiment of the present invention from 1 to 15 wt.-% (weight of particles/weight of pretreated lignocellulose-containing biomass material) of particles are added to the lignocellulose-containing biomass-material. In alternative embodiments:
  from 1 to 12 wt.-%;
  from 2 to 11 wt.-%; or
  from 3 to 10 wt.-%
are added.

Within a one embodiment, the particles are selected from the group consisting of graphite, charcoal, activated coal, silicate, clay mineral particles and mixtures thereof. In one embodiment, the particles are selected from graphite, charcoal and/or activated coal. To add particles from this group of materials is advantageous as the particles will substantially increase the energy value of the lignocellulose-containing biomass-material as the remaining or remnant material is usually used as combustible material for various applications. Suitable clay mineral particles are selected from the group consisting of bentonites and smectic sheet silicates, such as montmorillonite, aliettite, corrensite, kulkeite, lunijianlaite, rectorite, saliotite, tarasovite, tosudite, beidellite, brinrobertsite, nontronite, swinefordite, volkonskoite, yakhontovite, hectorite, ferrosaponite, saponite, sauconite, spadaite, stevensite, zincsilite and mixtures thereof.

Within another embodiment of the present invention, the particles added are selected from the particle-fraction separated according to step c). It is thereby possible that all of the particles added are selected from the particle fraction separated according to step c) or only a part of the particles added are selected from the particle fraction separated according to step c). In one embodiment, all particles separated are added to the biomass material. In alternative embodiments only a part of the particle-fraction separated according to step c) is added. In varying embodiments:
  at least 50 wt.-%;
  at least 65 wt.-%;
  at least 95 wt.-%; or
  at least 99 wt.-% are added. In a further embodiment from 50 to 99 wt.-% of the particles separated according to step c) are added. In alternative embodiments either from 65 to 99 wt.-% or from 85 to 99 wt.-% are added.

Within a further embodiment of the process of the present invention, it is also possible that part of the particles added are selected from the group consisting of graphite, charcoal, activated coal, silicate and clay mineral particles and another part is selected from the particles separated according to step c) of the inventive process. Within one embodiment at least 65 wt.-% (weight of particles from step c)/total weight of added particles) of the particles added are selected from the particles separated according to step c). In alternative embodiments: at least 85 wt.-%; or at least 95 wt.-% are selected, whereas the remaining amount of at most 15 wt.-%, is selected from charcoal, graphite, clay minerals and mixtures thereof. In an alternative embodiment the remaining amount at most 5 wt.-% is selected from charcoal, graphite, clay minerals and mixtures thereof.

Within a further embodiment, the particles added show a volumetric particle size distribution with a D(0.10) value of from 20 to 175 μm and a D(0.50) value from 250 to 450 μm. In one embodiment, the particle size distribution shows a D(0.10) value of from 35 to 130 μm and a D(0.50) value from 300 to 450 μm and. The particle size distribution was measured with a 5917 Mastersizer 2000 Ver. 5.40 (Serial number MAL1015917), by Malvern Instruments, UK.

In the following an exemplary embodiment of the present invention is described. The exemplary embodiment is not to be understood as limiting the invention in any respect.

EXEMPLARY EMBODIMENT

Process for the decomposition of lignocellulose-containing biomass-material selected from straw or bagasse, comprising the steps
(a) providing the lignocellulose-containing biomass-material;
(b) subjecting the lignocellulose-containing biomass-material to comminution selected from milling, shredding and grinding;
(c) subjecting the comminuted lignocellulose-containing biomass-material to a sifting to separate a particle-fraction consisting of particles with an average particle diameter of less than 2500 μm or less than 1800 μm;
(d) subjecting the remaining comminuted lignocellulose-containing biomass-material to a pretreatment selected from steam explosion;
wherein during pretreatment from 8 to 10 wt.-% particles are added to the lignocellulose-containing biomass-material wherein at least 85 wt.-% of the particles added have an average particle diameter of less than 1.6 mm and are selected from the particles separated according to step c).

EXAMPLES

The present invention is further described by the following example and figure. The example and figure are for illustrative purposes only and are not to be understood as limiting the invention.

Example 1

Rectangular wheat straw bales were transported with a conveyor system to a machine where the attached ribbons were removed. Next, the bales were loosened up in a bale crusher equipped with rotating scrappers operated at 3000 rpm yielding particles with particle sizes from 10 to 40 cm. This operation is needed to ensure a smooth transport of the straw and operation of the subsequent milling step. Next, the straw was pneumatically transported to a hammer mill operated at 3000 rpm with 30 mm sieves where the straw was cut to pieces with particle sizes from 1 to 5 cm. During the milling particles with a volumetric particle size distribution with a D(0.50) of 419 μm and particle sizes <2500 μm were removed with an aspiration system operated with a radial ventilator (model BWA-MXE, Reitz). The air containing these particles was then guided to a separator/filter system (bag filter model FTT 1-1-6, Hainke) where the particles were separated from the air. These particles were then put into a transport screw and transported to a buffer vessel.

The cut straw was transported to the thermal pretreatment system with a pin drum feeder follow by a transportation screw and plug screw. The screw system had an average power consumption of 12.1 kW. Next, the wheat straw was pretreated at 160° C. for 5 min without addition of any chemicals. The pretreated material was collected in a cyclone after thermal pretreatment.

The particles with the volumetric particle size distribution with a D(0.50) of 419 μm (see FIG. 2) where then mixed with the cut straw fraction by introducing them into the pneumatic straw transport system. This was done by use of a rotary feeder.

This method lead to power savings in the range of from 3 to 5.4% in power consumption (shown in FIG. 1) as the average power consumption of the screw transportation system of the thermal pretreatment unit dropped to 11.7 kW.

What is claimed is:

1. A process for the decomposition of lignocellulose-containing biomass-material, comprising the steps:
   (a) providing lignocellulose-containing biomass-material;
   (b) subjecting the lignocellulose-containing biomass-material to comminution, whereby a plurality of particles of the biomass-material are formed;
   (c) sifting the comminuted lignocellulose-containing biomass-material to obtain a particle-fraction having an average particle diameter of less than 2500 μm and remaining comminuted lignocellulose-containing biomass-material; and
   (d) subjecting the remaining comminuted lignocellulose-containing biomass-material to a pretreatment;
   wherein before, during or after the pretreatment, particles of said particle fraction or other particles are added to the remaining comminuted lignocellulose-containing biomass-material, wherein at least 70 wt.-% of the particles added have an average particle diameter of less than 1.6 mm, and wherein the particles added have a volumetric particle size distribution with a D(0.10) value of from 20 to 175 μm and a D(0.50) value from 250 to 450 μm.

2. The process of claim 1, wherein the particles added are added continuously during the pretreatment.

3. The process of claim 1, wherein particles are added to the remaining comminuted lignocellulose-containing biomass-material in an amount from 1 to 15 weight %, wherein the weight of the pretreated lignocellulose-containing biomass-material represents 100%.

4. The process of claim 1, wherein the particles added comprise one or more types of particles selected from the group consisting of graphite, charcoal, activated coal, silicate and clay mineral particles.

5. The process of claim 1, wherein the pretreatment is selected from mechanical pretreatment, biological pretreatment, chemical pretreatment, physical pretreatment and combinations thereof.

6. The process of claim 1, wherein the particles added are obtained from the particle-fraction separated from the comminuted lignocellulose-containing biomass-material according to step c).

7. The process of claim 1, wherein the particle-fraction separated from the comminuted lignocellulose-containing biomass-material in step c) has an average particle diameter of less than 1600 μm.

8. The process of claim 1, wherein at least 85 wt.-% of the particles added have an average diameter of less than 1.6 mm.

9. The process of claim 2, wherein particles are added to the remaining comminuted lignocellulose-containing biomass-material in an amount from 1 to 15 weight %, wherein the weight of the pretreated lignocellulose-containing biomass-material represents 100%.

10. A process for the decomposition of lignocellulose-containing biomass-material, comprising the steps:
   (a) providing lignocellulose-containing biomass-material;
   (b) subjecting the lignocellulose-containing biomass-material to comminution, whereby a plurality of particles of the biomass-material are formed;
   (c) sifting the comminuted lignocellulose-containing biomass-material to obtain a particle-fraction consisting of particles having an average particle diameter of less than 2500 μm and a remaining comminuted lignocellulose-containing biomass-material;
   (d) subjecting the remaining comminuted lignocellulose-containing biomass-material to a pretreatment;

wherein before, during or after pretreatment particles of said particle fraction or other particles are added to the remaining comminuted lignocellulose-containing biomass-material wherein at least 70 wt.-% of the particles added have an average particle diameter of less than 1.6 mm, wherein the particles added are characterized by a volumetric particle size distribution with a D(0.10) value from 20 to 175 μm and a D(0.50) value from 250 to 450 μm;

wherein the particles added are added continuously during the pretreatment;

wherein particles are added to the remaining comminuted lignocellulose-containing biomass-material in an amount from 1 to 15 weight %, wherein the weight of the pretreated lignocellulose-containing biomass-material represents 100%;

wherein the particles added comprise one or more types of particles selected from the group consisting of graphite, charcoal, activated coal, silicate and clay mineral particles;

wherein the pretreatment is selected from mechanical pretreatment, biological pretreatment, chemical pretreatment, physical pretreatment and combinations thereof.

11. The process of claim 10, wherein the particle-fraction obtained from the comminuted lignocellulose-containing biomass-material in step c) has an average particle diameter of less than 1600 μm.

12. The process of claim 10, wherein at least 85 wt.-% of the particles added have an average diameter of less than 1.6 mm.

* * * * *